(12) United States Patent
Stein et al.

(10) Patent No.: US 11,911,768 B2
(45) Date of Patent: Feb. 27, 2024

(54) TEST ELEMENT SUPPORT

(71) Applicant: Roche Diagnostics Operations, Inc., Indianapolis, IN (US)

(72) Inventors: Reiner Stein, Bad Kreuznach (DE); Martin Mertens, Schriesheim (DE); Werner Heidt, Darmstadt (DE)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 227 days.

(21) Appl. No.: 16/380,195

(22) Filed: Apr. 10, 2019

(65) Prior Publication Data
US 2019/0232292 A1 Aug. 1, 2019

Related U.S. Application Data

(63) Continuation of application No. PCT/EP2017/076028, filed on Oct. 12, 2017.

(30) Foreign Application Priority Data

Oct. 14, 2016 (EP) .................................... 16193896

(51) Int. Cl.
*B01L 7/04* (2010.01)
*B01L 9/00* (2006.01)
(Continued)

(52) U.S. Cl.
CPC ........ *B01L 7/04* (2013.01); *B01L 9/52* (2013.01); *G01N 21/84* (2013.01);
(Continued)

(58) Field of Classification Search
CPC ...... B01L 7/04; B01L 9/52; B01L 2300/0609; B01L 2300/0663; B01L 2300/08;
(Continued)

(56) References Cited

U.S. PATENT DOCUMENTS 4,301,412 A 11/1981 Hill et al.
5,789,664 A 8/1998 Neel et al.
(Continued)

FOREIGN PATENT DOCUMENTS

DE 102013211693 B3 7/2014
JP H03-296292 A 12/1991
(Continued)

OTHER PUBLICATIONS

Xu, Lei, et al. "A low power catalytic combustion gas sensor based on a suspended membrane microhotplate." 2011 6th IEEE International Conference on Nano/Micro Engineered and Molecular Systems. IEEE, 2011. (Year: 2011).*
(Continued)

*Primary Examiner* — Robert J Eom
(74) *Attorney, Agent, or Firm* — Woodard, Emhardt, Henry, Reeves & Wagner, LLP

(57) ABSTRACT

A test element support comprises a heating element for heating a test element for analytical examination of a sample. The heating element comprises a substrate, which is made of at least one substrate material. The substrate comprises at least one active area configured for being heated and at least one non-active area outside the active area. The active and the non-active areas are separated by at least one thermal insulation element. The thermal insulation element has a lower thermal conductivity than the substrate material. The thermal insulation element is fully or partially embedded into the substrate. The test element support further comprises at least one heater. The heater comprises at least one heater substrate and the heater substrate is attached to the substrate, wherein the heater substrate is attached to a back face of the substrate. The back face opposes a front face of the substrate contacting the test element.

16 Claims, 3 Drawing Sheets

(51) Int. Cl.
  *G01N 21/84* (2006.01)
  *G01N 27/327* (2006.01)
  *G01N 33/487* (2006.01)
  *G01N 33/49* (2006.01)
  *H05K 1/02* (2006.01)
  *H05K 1/14* (2006.01)
  *H05K 3/36* (2006.01)

(52) U.S. Cl.
  CPC ... *G01N 27/3271* (2013.01); *G01N 33/48707* (2013.01); *G01N 33/4905* (2013.01); *H05K 1/0212* (2013.01); *H05K 1/144* (2013.01); *H05K 3/368* (2013.01); *B01L 2300/0609* (2013.01); *B01L 2300/0663* (2013.01); *B01L 2300/08* (2013.01); *B01L 2300/1805* (2013.01); *B01L 2300/1883* (2013.01); *H05K 2201/041* (2013.01); *H05K 2201/062* (2013.01); *H05K 2201/09063* (2013.01); *H05K 2201/10151* (2013.01); *H05K 2203/1115* (2013.01)

(58) Field of Classification Search
  CPC ..... B01L 2300/1805; B01L 2300/1883; G01N 21/84; G01N 27/3271; G01N 33/48707; G01N 33/4905; H05K 1/0212; H05K 1/144; H05K 3/368; H05K 2201/041; H05K 2201/062; H05K 2201/09063; H05K 2201/10151; H05K 2203/1115
  See application file for complete search history.

(56) References Cited

U.S. PATENT DOCUMENTS

| 6,423,940 | B1 | 7/2002 | Schupbach |
| 2006/0035298 | A1 | 2/2006 | Hill et al. |

FOREIGN PATENT DOCUMENTS

| WO | 1995/007452 | A2 | 3/1995 |
| WO | 2000/006761 | A1 | 2/2000 |
| WO | 2003/103006 | A2 | 12/2003 |
| WO | 2005/027578 | A1 | 3/2005 |
| WO | 2006/058324 | A1 | 6/2006 |
| WO | 2009/052222 | A1 | 4/2009 |

OTHER PUBLICATIONS

Hoenes, Joachim et al., The Technology Behind Glucose Meters: Test Strips, Diabetes Technology & Therapeutics, 2008, pp. S-10-S-26, vol. 10, Supplement 1.

International Search Report in Application No. PCT/EP2017/076028 dated Jan. 9, 2018, 15 pages.

* cited by examiner

TEST ELEMENT SUPPORT

CROSS-REFERENCE TO RELATED APPLICATIONS

This application is a continuation of International Patent Application No. PCT/EP2017/076028, filed 12 Oct. 2017, which claims the benefit of European Patent Application No. 16193896.4, filed 14 Oct. 2016, the disclosures of which are hereby incorporated herein by reference in their entirety.

TECHNICAL FIELD

The present disclosure relates to a test element support and a test element analysis system for the analytical examination of a sample. The disclosure further relates to a method for manufacturing at least one test element support, the test element support comprising at least one heater and at least one heating element being configured for heating a test element for analytical examination of a sample. The devices and methods according to the present disclosure mainly may be used in the field of qualitatively or quantitatively detecting at least one analyte in a sample, such as a sample of a body fluid, and/or for determining at least one parameter of the sample. Other fields of application are feasible.

BACKGROUND

In the field of medical technology and diagnostics, a large number of devices and methods for determining the presence and/or the concentration of one or more analytes in samples, specifically fluid samples, such as body fluids, and/or for determining at least one parameter of a sample are known. Without restricting the scope of the present disclosure, in the following, mainly reference is made to the determination of coagulation parameters or analyte concentrations in blood samples, e.g., glucose concentrations. As an example, reference may be made to commercially available devices and systems, such as the CoaguChek® XS, CoaguChek® XS Pro, CoaguChek® Pro II or CoaguChek® INRange systems, the Reflotron system or to the cobas h 232 system, all by Roche Diagnostics GmbH, Germany. It shall be noted, however, that other types of samples or other types of analytes or parameters may be used in a similar way.

For performing fast and simple measurements, several types of test elements are known, which mainly are based on the use of one or more test chemicals, i.e., on the use of one or more chemical substances, one or more chemical compounds or one or more chemical mixtures, adapted for performing a detection reaction for detecting the analyte or determining the parameter. The test chemical often is also referred to as a test substance, a test reagent, a test chemistry or as a detector substance. For details of potential test chemicals and test elements comprising such test chemicals, which may also be used within the present disclosure, reference may be made to J. Hoenes et al.: The Technology Behind Glucose Meters: Test Strips, Diabetes Technology & Therapeutics, Vol. 10, Supplement 1, 2008, S-10 to S-26. Other types of test elements and/or test substances are feasible and may be used within the present disclosure.

By using one or more test chemicals, a detection reaction may be initiated, the course of which depends on the presence and/or the concentration of the at least one analyte or on the parameter to be determined. The detection reaction typically may be analyte-specific. Typically, as may also be the case in the present disclosure, the test chemical is adapted to perform at least one detection reaction when the analyte is present in the body fluid, wherein the extent and/or the degree of the detection reaction typically depends on the concentration of the analyte. Generally, the test chemical may be adapted to perform a detection reaction in the presence of the analyte, wherein at least one detectable property of at least one of the body fluid and the test chemical is changed due to the detection reaction. The at least one detectable property generally may be selected from a physical property and a chemical property. In the following, without restricting potential other embodiments, reference will mainly be made to detection reactions in which one or more physical properties are changed due to the detection reaction, such as one or more of at least one electrical property and at least one optical property. Further, without restricting alternative solutions, reference will be made to detection reactions in which at least one chemical property which is electrically detectable is changed, i.e., to electrochemical test elements. Other test elements, such as optical test elements, however, are usable, too.

As generally known in the art of chemical analytics, the detection reaction and, thus, the measurement result may strongly depend on the temperature of the test element, specifically on the temperature in a reaction zone or measurement zone of the test element, and/or of the sample. A precise temperature control of the test element and/or a precise monitoring of the temperature of the test element is therefore desirable, in order to increase the accuracy of the measurement. Therefore, several known devices generally provide a heating device for heating the test element.

Therein, however, a technical challenge resides in providing a high degree of homogeneity of temperature over an active area of a heating element for the test elements. The technical challenges generally rise with the size of the heating element. Thus, in large area heating elements having only a small active area, typically, many alternative heat paths may be present, such as paths of heat transport via mounting parts, holding down clamps for the test strip or the like. In these setups, achieving a homogeneous temperature distribution is generally rather difficult. Further, the larger the heating element is, the more energy is needed to heat up the system to a desired temperature. The amount of energy required for heating up the system to a target temperature generally imposes a challenge specifically for handheld devices, due to the limited capacity and lifetime of commercially available batteries. Additionally, not only the amount of energy increases, but also the heat-up-time. This leads to a longer waiting time for the user of such instruments.

BRIEF SUMMARY

It is against the above background that the embodiments of the present disclosure provide certain unobvious advantages and advancements over the prior art. In particular, the inventors have recognized a need for improvements in a test element support, a test element analysis system and a method for manufacturing a test element support.

Although the embodiments of the present disclosure are not limited to specific advantages or functionality, it is noted that the present disclosure ensures a homogeneous heating of an active area, with a sufficient thermal contact between the active area and the test element to be heated by the test element support comprising at least one heater and at least one heating element.

In accordance with one embodiment of the present disclosure, a test element support is provided, wherein the test element support comprises at least one heating element for heating a test element for analytical examination of a sample, the heating element having a substrate, the substrate being made of at least one substrate material, the substrate comprising at least one active area configured for being heated and at least one non-active area outside the active area, the active area and the non-active area being separated by at least one thermal insulation element, wherein the thermal insulation element has a lower thermal conductivity than the substrate material, wherein the thermal insulation element is fully or partially embedded into the substrate, wherein the test element support further comprises at least one heater, wherein the heater comprises at least one heater substrate, wherein the heater substrate is attached to the substrate, wherein the heater substrate is attached to a back face of the substrate, the back face opposing a front face of the substrate contacting the test element, wherein the active area of the heating element forms an integrated heating surface of the test element support.

In accordance with another embodiment of the present disclosure, a test element analysis system for the analytical examination of a sample is provided, the test element analysis system comprising at least one test element receptacle, wherein the test element analysis system further comprises at least one test element support according to an embodiment of the present disclosure, wherein the test element support is arranged to heat at least one test element received at least partially in the test element receptacle.

In accordance with yet another embodiment of the present disclosure, a method for manufacturing at least one test element support is provided, the test element support comprising a heating element which is configured for heating at least one test element, the test element being configured for analytical examination of a sample, the method comprising: a) providing a substrate, the substrate being made of at least one substrate material, b) providing at least one active area within the substrate, the active area being configured for being heated, c) providing at least one non-active area within the substrate, the non-active area being located outside the active area, d) providing at least one thermal insulation element separating the non-active area and the active area, wherein the thermal insulation element has a lower thermal conductivity than the substrate material, wherein the thermal insulation element is fully or partially embedded into the substrate, e) providing at least one heater having at least one heater substrate, and f) attaching the heater substrate to a back face of the substrate, the back face opposing a front face of the substrate contacting the test element, wherein the active area of the heating element forms an integrated heating surface of the test element support.

These and other features and advantages of the embodiments of the present disclosure will be more fully understood from the following description in combination with the drawings and the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Figure 1:
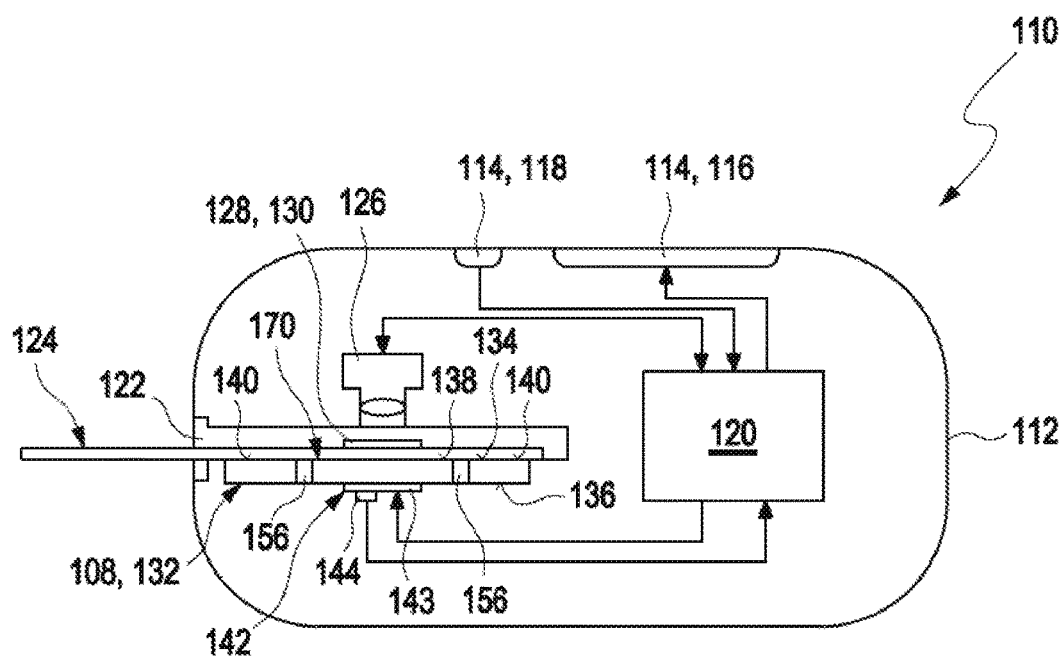
FIG. 1 shows an exemplary embodiment of a test element analysis system.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, notwithstanding the fact that the respective feature or element may be present once or more than once.

Further, as used in the following, the terms "preferably", "more preferably", "particularly", "more particularly", "specifically", "more specifically", "typically", "more typically", or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in such way with other optional or non-optional features of the disclosure.

In a first aspect of the present disclosure, a test element support is disclosed. The test element support comprises at least one heating element for heating a test element, the test element being configured for analytical examination of a sample. The heating element comprises a substrate, wherein the substrate is fully or partially made of at least one substrate material. The substrate comprises at least one active area configured for being heated and at least one non-active area outside the active area. The active area and the non-active area are separated by at least one thermal insulation element. The thermal insulation element has a lower thermal conductivity than the substrate material. The thermal insulation element is fully or partially embedded into the substrate. Further, the test element support comprises at least one heater. The heater comprises at least one heater substrate. The heater substrate is attached to the substrate. The heater substrate is attached to a back face of the substrate opposing a front face of the substrate contacting the test element.

As further used herein, the term "test element support" refers to an arbitrary element which is configured to bear or to hold up a test element. The test element support may specifically comprise at least one surface which serves as a supporting surface for the test element. Specifically, the front face of the substrate may form a supporting surface for the test element. Thus, the test element may be in direct contact with the test element support via the supporting surface. The test element support may provide a mechanical support for the test element. Thus, the test element support may be configured to hold the test element in a desired position. Further, the test element support may be configured to prevent the test element from a movement in at least one direction. The test element support may be part of the test element analysis system as will further be outlined below in more detail. When the test element is located on the test element support, the test element analysis system may be configured to detect at least one analytical reaction of the sample with at least one test chemical comprised by the test element. The test element may exemplarily be a test strip as will further be outlined below and the test element support may also be referred to as "test strip support".

The test element support may specifically be a flat test element support. The term "flat test element support" may generally refer to an arbitrary test element support which comprises at least one flat surface. The flat surface may specifically correspond to a supporting surface of the test element support configured for holding up the test element. Further details on the flat surface are provided below in more detail.

As outlined above, the test element support comprises the at least one heating element. As used herein, the term "heating element" refers to an arbitrary element, device or combination of devices configured for providing an amount of heat to another element or device. As outlined in further detail below, the heating element specifically may be an electrical heating element, having at least one electrical heater, such as a resistive heater. In order to be used as a heating element for heating a test element, the heating element specifically may comprise at least one heater surface configured for directly or indirectly contacting the test element. The test element specifically may be a test strip, so the heating surface specifically may be a flat heating surface.

The term "test element" generally may refer to an arbitrary device which is capable of detecting the analyte in the sample or of determining the parameter of the sample. The test element may specifically be a strip-shaped test element. As used herein, the term "strip-shaped" refers to an element having an elongated shape and a thickness, wherein an extension of the element in a lateral dimension exceeds the thickness of the element, such as by at least a factor of 2, typically by at least a factor of 5, more typically by at least a factor of 10, and most typically by at least a factor of 20 or even at least a factor of 30. Thus, the test element may also be referred to as test strip.

As further used herein, the term "sample" may refer to an arbitrary material or combination of materials taken for an analysis, testing or investigation. The sample may be a limited quantity of something which is intended to be similar to and may represent a larger amount. However, the sample may also comprise a full specimen. The sample may be a solid sample, a liquid sample or a gaseous sample or a combination of these. Specifically, the sample may be a fluid sample, i.e., a sample which is fully or partially in a liquid state and/or in a gaseous state. A quantity of the sample may be describable in terms of its volume, mass or size. However, other dimensions are feasible. The sample may comprise only one material or only one compound. Alternatively, the sample may comprise several materials or compounds.

The test element specifically may be configured for qualitatively or quantitatively detecting at least one analyte in the sample and/or for determining at least one parameter in the sample. The term "analyte", as will be used and discussed in further detail below, generally refers to an arbitrary element, component or compound which may be present in the sample and the presence and/or the concentration may be of interest for the user, the patient or medical staff such as a medical doctor. Particularly, the analyte may be or may comprise an arbitrary chemical substance or chemical compound which may take part in the metabolism of the user or the patient, such as at least one metabolite. The detection of the at least one analyte specifically may be an analyte-specific detection. The term "parameter" generally may refer to an arbitrary value such as a measurement value which is obtainable within or by an analytical test. Exemplarily, the parameter may correspond to a property of the sample and/or a property of the at least one analyte as described above. Specifically, the parameter may be a coagulation parameter such as to a coagulation time of a blood sample. For further details on the term "coagulation parameter" as further used herein, reference may be made to US 2006/0035298, the disclosure of which is hereby incorporated herein by reference.

The sample specifically may be or may comprise at least one body fluid, also referred to as a bodily fluid. As used herein, the term "body fluid" may refer to a fluid which typically is present in a body or body tissue of the user or the patient and/or which may be produced by the body of the user or the patient. As an example for body tissue, interstitial tissue may be named. Thus, as an example, the body fluid may be selected from the group consisting of blood and interstitial fluid. However, additionally or alternatively, one or more other types of body fluids may be used, such as saliva, tear fluid, urine or other body fluids.

The term "analytical examination" generally may refer to a process of determining the presence and/or the quantity and/or the concentration of the at least one analyte or to a process of determining a parameter of the sample which is characteristic of the properties of the sample, e.g., a coagulation parameter which is characteristic of the coagulation properties of a blood sample. The detection may be or may comprise a qualitative detection, simply determining the presence of the at least one analyte or the absence of the at least one analyte, and/or may be or may comprise a quantitative detection, which determines the quantity and/or the concentration of the at least one analyte. As a result of the detection, at least one signal may be produced which characterizes an outcome of the detection, such as at least one measurement signal. The at least one measurement signal specifically may be or may comprise at least one electronic signal such as at least one voltage and/or at least one current. The at least one signal may be or may comprise at least one analogue signal and/or may be or may comprise at least one digital signal.

The term "substrate", as used herein, generally refers to a basic element giving the heating element its shape and stability. The substrate may be or may comprise a carrier or base plate which, as will be outlined in further detail below, may carry one or more further elements. The substrate may be made of one piece or may comprise multiple components. The substrate, as will be outlined in further detail below, specifically may have the shape of a plate or disk and/or may have one or more plane surfaces. Other shapes, however, are feasible.

As further used herein, the term "substrate material" generally refers to a material, a mixture of materials or a plurality of materials of which the substrate is fully or partially composed of. The substrate material, as will be outlined in further detail below, specifically may be or may comprise at least one rigid material. Specifically, the substrate material may be or may comprise at least one of a metal, including pure metals or metal alloys, a plastic material, a ceramic material or a composition of materials, such as a laminated material. Other options, however, are feasible.

As further used herein, the term "active area" generally refers to an area contacting the test element and intended for transferring heat to the test element. A temperature of the active area may be controlled. Thus, the active area may be a real or virtual region, volume or surface area the temperature of which may be adjusted to at least one distinct and predetermined or determinable temperature value, which may be transferred to the test element contacting the full active area or a part thereof.

Consequently, the term "non-active area" generally refers to an area outside the active area. Thus, again, the non-active area may be a real or virtual area of the substrate. As used herein, the term "virtual area" generally refers to an area defined by its function of being heated or not. Apart from this function and configuration of being heated or not, the active area necessarily has to be distinguished from the non-active area structurally.

The active area and the non-active area specifically may be or may comprise areas of a surface of the heating element, such as a heating surface facing the test element. The heating surface specifically may fully or partially be designed as a flat heating surface. Still, other embodiments are feasible. Thus, the active and non-active areas may also be partial volumes of the substrate. In the latter case, the active area may comprise at least one active surface area facing the test element, and the non-active area may optionally also comprise at least one non-active surface area. The active area and the non-active area may be located in one plane of the heating element, specifically in one plane of the test element support. As outlined above, the active area is configured for being heated. Thus, the active area may be configured for transferring heat to the test element as well as for providing mechanical support for the test element. The non-active area may provide an additional mechanical support for the test element and may thus increase a supporting area for the test element.

As further used herein, the term "being separated" refers to the fact that the two elements which are separated are distinct and located apart from one another with a separating element in between the two elements. Thus, the thermal insulation element is located in between the at least one active area and the at least one non-active area. In case a plurality of active areas and/or a plurality of non-active areas are provided, at least one thermal insulation element is located in between at least one active area and at least one non-active area. As an example, precisely one active area may be provided, which fully or partially is surrounded by precisely one non-active area, with at least one thermal insulation element located on at least one virtual borderline in between the active area and the non-active area. Alternatively, at least two active areas may be interleaved by at least one non-active area, with thermal insulation elements in between the nonactive area and the two active areas. Alternatively, again, at least two non-active areas may be interleaved by at least one active area, with thermal insulation elements in between the active area and the two non-active areas. Further exemplary embodiments will be given below.

As further used herein, the term "thermal insulation element" refers to an arbitrary element which is suited to impede a heat flow in between two elements separated by the thermal insulation element, as compared to a situation in which no thermal insulation element is given in between the two elements, such as compared to a situation in which the two elements are in direct thermal or physical contact with one another. Thus, as an example, in case the active area is heated to a higher temperature than the non-active area, in case the thermal insulation element is provided in between these areas, a thermal equilibrium in between the two areas, such as a state in which the two areas have the same temperature, will be reached at a later point in time as compared to the situation in which no thermal insulation element is provided in between these areas, such as with the areas being in direct physical or thermal contact with each other.

As further used herein, the term "thermal conductivity" refers to the capability of a material of conducting heat. The thermal conductivity may be anisotropic or, typically, isotropic. The unit often used for the thermal conductivity is $W/(m \cdot K)$. The reciprocal value of the thermal conductivity is often referred to as the thermal resistivity.

As further used herein, the term "embedded" refers to the situation in which one element is fully or partially surrounded or enclosed by another element. Thus, the embedded element may be in direct contact with the embedding element and may be fully or partially surrounded by the embedding element. The elements may form one single entity.

The thermal insulation element generally may have an arbitrary physical state. Thus, the thermal element may fully or partially be made of one or more of a solid material, a gaseous material or a liquid material. Thus, as an example, the thermal insulation element may also comprise a void in the substrate, wherein the void also may fully or partially be filled with gas, such as air, or a vacuum. The thermal insulation element, however, specifically may comprise at least one hole in the substrate, wherein the hole specifically may be filled with one or more gases, such as air. Typically, the hole may be selected from the group consisting of a round hole, a polygonal hole, a slot, an elongated hole. Thus, as an example, the thermal insulation element specifically may comprise a round hole in the substrate and/or an elongated slot. Thus, the active area and the non-active area may be separated specifically by one or more hole in the substrate. The thermal insulation element specifically may comprise at least two holes, typically at least three holes, wherein the holes, specifically, may be located in a row. A cross-sectional area of the substrate may be reduced by the insulation element, specifically by the hole. Specifically, the cross-sectional area of the substrate may be reduced by at least 15%, typically by at least 25%, more typically by at least 35%, more typically by at least 50%, more typically by at least 65%, more typically by at least 75%, more typically by at least 85%, more typically by at least 90% and most typically by at least 95%. Further, the cross-sectional area may be reduced by the insulation element by 100%.

Thereby, an insulation material may exemplarily be placed in the hole, which fully extends along the cross-section of the substrate. Thus, as an example, a cross-section of the substrate through a borderline of the active area may be taken. Along the borderline, one or more thermal insulation elements may be located, which may comprise one or more holes which may be filled with air or with another thermally insulating material. The cross-section is taken through the one or more holes, and the cross-sectional area of the substrate with the holes is compared with the theoretical situation without holes. The above mentioned reduction of the cross-sectional area by the holes, including the exemplary values give, may apply to this situation. The hole may specifically comprise rounded edges. Thus, a tilting of the test element during insertion may be avoided.

The substrate may comprise at least one essentially flat front face, such as a front face facing the test element, and at least one essentially flat back face, wherein the void may extend from the front face to the back face. Thus, the void specifically may be or may comprise a through hole, extending from the front face to the back face, the hole having one of the shapes listed above.

The insulation element may fully or partially be made of at least one material selected from the group consisting of: air, a plastic material, a ceramic material, a composite material, such as a foam material. It shall be noted, however, that other materials are feasible, too. As will be outlined in further detail below, the use of air specifically simplifies the production of the thermal insulation element, since the thermal insulation element simply may be made e.g., by producing a through hole through the substrate, the through hole being filled with air.

The active area specifically may fully or partially be surrounded by a virtual or non-virtual borderline. The at least one thermal insulation element specifically may be located on the borderline. In case a plurality of thermal insulation elements is provided, the thermal insulation element specifically may be located in a row on the borderline. The borderline may be a closed borderline, such as a circle, a rectangle, a polygon or an oval, or may be an open borderline, such as a straight, bent or curved borderline. In case the borderline is a closed borderline, the at least one thermal insulation element may be provided on one side of the borderline or a plurality of sides of the borderline.

As outlined above, the test element support further comprises the at least one heater. The heater specifically may be in contact with the substrate or substrate material. Specifically, the heater may be located on the back face, as will be outlined in further detail below. As used herein, the term "heater" refers to an arbitrary element which is designed or configured to produce heat, e.g., by transforming one or more types of energy other than heat into heat. Specifically, the heater may be an element configured for transforming electrical energy into thermal energy, wherein the transformation may be a full transformation or a partial transformation. Thus, specifically, the heater may be or may comprise at least one thermal resistor, i.e., an electrical element having an electrical resistivity configured for producing heat in case a current flows through the element.

The heater comprises at least one heater substrate, wherein the heater substrate is attached to the substrate of the heating element. The heater substrate may be attached to the back face of the substrate, the back face opposing the front face of the substrate contacting the test element. The heater substrate specifically may comprise at least one material selected from the group consisting of a flexible circuit board and a circuit board.

Further, the heater may be located in an area opposing the test element. Specifically, the heater may be located in an area opposing the active area of the substrate. Thereby, the active area may be in contact, specifically in direct contact, with the test element. Thus, the heater may be configured to heat the active zone of the substrate selectively.

Further, the heater may be configured to be directly applied on the substrate of the heating element without a separate heater substrate. Exemplarily, a heating structure may be configured to be directly printed to the heater substrate. The heater specifically may comprise at least one electrical connector for electrically contacting the heater.

The heater specifically may be embodied fully or partially as a printed circuit board, typically a flexible printed circuit board. Still, rigid printed circuit boards are feasible, too. As an example, a thermal resistor may be located on a flexible printed circuit board, and the flexible printed circuit board may be located on a back face of the substrate, specifically in an area opposing the active area contacting the test element.

The heating element and, specifically, the heater, may comprise at least one thermal sensor element. As used herein, the terms "thermal sensor element" generally refers to an arbitrary element which is configured to provide at least one signal indicative of a temperature. The thermal sensor element specifically may fully or partially be integrated into the heater. Additionally or alternatively, however, the thermal sensor element may also be located in a different part of the heating element. The thermal sensor element, as an example, may be integrated into a printed circuit board, such as into a flexible printed circuit board, which may also comprise the heater. As outlined above, the printed circuit board specifically may be attached to the substrate, such as on a back face of the substrate.

The substrate and/or the heater substrate specifically may be essentially flat. Thus, as an example, the substrate and/or the heater substrate may have the shape of a disc, with two opposing surfaces which are substantially parallel, such as with a tolerance of no more than 20°, typically of no more than 10°, more typically of no more than 5°. These parallel surfaces specifically may fully or partially be flat, wherein grooves or other structural elements may also be provided on these surfaces. These surfaces may form the above-mentioned front face and back face of the substrate. The thickness of the substrate may be smaller than a typical lateral extension of the substrate in a plane of the front face and/or back face, e.g., a diameter or equivalent diameter of the front face and/or back face. Thus, as an example, a thickness of the substrate in a direction perpendicular to the front face and/or back face may be smaller by at least a factor of 2, typically at least a factor of 5, and more typically at least a factor of 10 or at least a factor of 20, than the equivalent diameter of the front face and/or back face.

Specifically, the front face of the substrate of the heating element may comprise an essentially flat surface. The term "flat surface" may specifically refer to an even surface or to a planar surface which is at least to a large extent free from unevennesses such as protrusions and/or grooves. Specifically, at least 90% of the surface, typically at least 95% of the surface and more typically at least 99% of the surface may be free from unevenesses. Specifically, the front face of the substrate may be essentially free from protrusions. The term "protrusion" may refer to an element which emerges from a surface. Specifically, at least 90% of the front face, typically at least 95% of the front face and more typically at least 99% of the front face may be free from protrusions. Thus, the front face may also be referred to as smooth surface. The flat surface may form a supporting surface for the test element. Thus, the flat surface may be configured to hold up the test element. The test element may specifically have at least one flat test element surface which is configured to be laid up on the front face of the heating substrate. The test element, specifically the flat test element surface, may be in direct contact with the flat surface of the substrate, specifically with a front face surface of the front face of the heating substrate. The test element surface and the front face surface of the heating substrate may be arranged substantially parallel to each other, such as with a tolerance of no more than 20°, typically of no more than 10°, more typically of no more than 5°.

Due to the parallel orientation of the front surface of the substrate of the heating element and the test element surface a tilting of the test element during insertion within a test element receptacle as will further be described below in more detail, may be prevented or reduced at least to a large extent. Thus, a smooth insertion may be feasible and a damaging of the test element may be avoided. Thus, a receiving of a reliable measurement may be ensured.

Further, the heater substrate may comprise an essentially flat heater substrate surface. The flat heater substrate surface may be in direct contact with a flat surface of the substrate, specifically with a back face surface of the back face of the heating substrate. The heater substrate surface and the back face surface of the heating substrate may be arranged substantially parallel to each other, such as with a tolerance of no more than 20°, typically of no more than 10°, more typically of no more than 5°. This may lead to an efficient heat transfer from the heater over the heating element to the test element.

The test element support may specifically be configured such that the test element lies on the front face of the substrate. Thus, the test element and the heater may be located on opposing sites of the substrate. Due to the arrangement of the heater and the test element on opposing sides of the substrate of the heating element, a flat surface may be provided on the front face of the substrate. Thus, the front face may be free from edges and/or protrusions. The test element may lie flatly on the front face surface, specifically on the active area of the heating element and an efficient heat transfer may be ensured. Further, as a heat transfer may be realized from below the test element, the heating element and/or the heater serve as a supporting element instead of laying on the test element. Thus, in contrast to a construction wherein the heating element and/or the heater are arranged on top of the test element, a loading of the test element due to a weight of components and thereby a potential deformation of the test element may be avoided.

The at least one thermal insulation element specifically may be essentially flush with at least one surface of the substrate, specifically with a front face and/or a back face of the substrate.

The substrate specifically may fully or partially be made of one or more of a plastic material, a metal or a ceramic material. As outlined above, other materials are feasible, too.

The heating element may further comprise at least one mounting element for mounting the heating element to at least one part of a test element analysis system. Specifically, the at least one mounting element may be or may comprise at least one mounting hole. The at least one mounting element specifically may be located fully or partially within the non-active area of the substrate. As an example, one or more than one mounting elements may be provided. Specifically, at least two, typically at least four, mounting elements may be provided. The substrate specifically may be a flat substrate having an essentially rectangular shape with at least two, typically at least four, protrusions or ears protruding from the rectangular shape, wherein the mounting elements are fully or partially located within the protrusions or ears.

The heating element may further comprise at least one connector region for electrically connecting the heating element to at least one electrical connector. The connector region specifically may be located in the non-active area.

The heating element, as outlined above, specifically may comprise at least one thermal sensor element. The thermal sensor element, as an example, may fully or partially be part of the heater and/or may fully or partially be integrated into a different part of the heating element. The thermal sensor element specifically may comprise at least one thermal resistor configured for measuring a temperature and/or at least one other type of electrical thermal sensor element. The heating element specifically may comprise at least two thermal sensor elements, wherein, as an example, at least one of the thermal sensor elements may be located within the active area and/or may be configured for measuring a temperature within the active area, and wherein at least another one of the thermal sensor elements may be located within the non-active area and/or may be configured for measuring a temperature within the non-active area.

The active area of the heating element may form an integrated heating surface of the test element support. The term "integrated heating surface" may refer to an arbitrary heating surface which is combined or embedded into another surface or which form one unit with the other surface. Specifically, the integrated heating surface may be embedded into the supporting surface of the test element support or may be part of the supporting surface. The supporting surface may comprise at least one surface of the substrate of the heating element such as the front face surface. The thermal insulation element may be essentially flush with the heating surface of the test element support. Thus, the integrated heating surface may provide a mechanical support of the test element and may allow a defined heating of the test strip at the same time. The heating may specifically only take place within the active area of the heating element and may be reduced within the non-active area. The test element support may have the active area and the non-active area being located in one plane. Consequently, a smooth insertion and an accurate positioning of the test element on the supporting surface may be feasible. Further, the thermal insulation element may be embedded in the integrated heating surface which may correspond to the supporting surface. Thus, an efficient thermal insulation may be ensured.

In a further aspect of the present disclosure, a test element analysis system for the analytical examination of a sample is disclosed. As used herein, the term "system" generally refers to an arbitrary set of interacting components or parts forming a whole or entity. Specifically, the components may interact with each other in order to fulfil at least one common function. The components may be handled independently or may be coupled or connectable to one another. Thus, generally, the term "test element analysis system" generally refers to a system configured for performing at least one analysis by using at least one test element. For potential definitions of the term "analysis", reference may be made to the term "analytical examination" as given above. Thus, the test element analysis system may generally refer to a system configured for determining the presence and/or the quantity and/or the concentration of at least one analyte and/or for determining at least one parameter of a sample which is characteristic of the properties of the sample. Thus, as an example, the concentration of at least one analyte may be determined by using the analysis system and, further, the test element, and/or a parameter such as a coagulation parameter may be determined.

The test element analysis system comprises at least one test element receptacle. As used herein, the term "test element receptacle" generally refers to a space of the test element analysis system, such as within a meter of the test element analysis system, also referred to as an analytical meter or measurement device, into which the test element may fully or partially be received and which may fully or partially surround the test element, in order to perform an analytical examination of the sample. Thus, as an example, the test element receptacle may comprise at least one slot and/or space in between a housing of the meter, into which the test element may be inserted from the outside of the meter and/or from a magazine within the meter. The slot, as an example, may be configured for holding the test element in such a way that a part of the test element protrudes from the meter, in order to apply the sample, and another part of the test element is received inside the meter, e.g., for performing the measurement. Other embodiments, however, are feasible.

The test element analysis system further comprises at least one test element support according to the present disclosure, such as according to one or more of the embodiments disclosed above and/or according to one or more of the embodiments disclosed in further detail below. The test element support comprises the heating element which is arranged to heat at least one test element received in the test element receptacle. Thus, the test element analysis system further comprises the heater. The heater may at least partially form the test element receptacle, e.g., a slot for inserting the test element, wherein the heating element is arranged inside the heater, with at least one front face facing the slot. As an example, the heating element, specifically the front face of the heating element, may form at least one side wall of a slot of the test element receptacle, such that a test element, inserted into the slot, is in contact with the front face.

The test element analysis system may further comprise at least one detector for detecting at least one analytical reaction of the sample with at least one test chemical comprised by the test element. Thus, the detector may be part of a meter of the test element analysis system. Depending on the properties of the test chemical and/or the test element, the detector may be adapted to the specific type of analytical reaction, also referred to as the detection reaction. As an example and as outlined in detail above, the analytical reaction specifically may be detectable by optical measurements and/or by electrical measurements. As an example, the test element may be one or more of an electrochemical test element and/or an optical test element. Thus, as an example, the at least one detector may be or may comprise at least one of an optical detector and/or an electrical detector. An optical detector, as an example, may comprise at least one light source for illuminating the test chemical, such as at least one test field comprising the at least one test chemical, and/or at least one optical sensor for detecting light propagating from the test chemical towards the detector, such as at least one photodiode or an imaging sensor like a CCD or CMOS device. Additionally or alternatively, the detector may comprise at least one current source and/or voltage source and at least one of a current measurement device and/or a voltage measurement device. These types of detectors and/or measurements are generally known to the skilled person.

As outlined above, the test element analysis system specifically may comprise at least one meter, the meter specifically having the at least one test element receptacle and, typically, the at least one detector. The test element analysis system, besides the at least one meter, may further comprise the at least one test element itself. The at least one test element specifically may be configured for performing at least one analytical reaction with the sample. The test element specifically may be a strip-shaped test element, e.g., a test strip, the test strip having at least one test field comprising the at least one test chemical. It shall be noted, however, that, generally, other types of test elements are usable, such as test elements having the shape of a tape and/or a disc.

The test element receptacle specifically may be arranged such that at least one test element received by the test element receptacle contacts both the at least one active area and the at least one non-active area of the heating element. Specifically, the test element analysis system may be configured such that a back side of the test element, which opposes the at least one test field, contacts an active area at the front face of the heating element, whereas at least one other part of the test element, such as a part outside the test field, contacts the non-active area. In embodiments of the disclosure, active areas may be located beneath other areas of the test elements like reaction zones or incubation zones, additionally or alternatively to the location beneath the test field of the test element. This is advantageous for embodiments in which the test element comprises different zones with different functions such as reaction zones, incubation zones or detection zones which need different temperature values. Such test elements may exemplarily be configured to be used for performing multi-step reactions on the test element.

As outlined above, the substrate material has a higher thermal conductivity than the thermal insulation element. Specifically, the thermal conductivity of the substrate material may be at least 5 times the thermal conductivity of the thermal insulation element, more typically at least 10 times and even more typically at least 100 times.

The substrate material may have a thermal conductivity of at least 1 W/(m·K), more typically a thermal conductivity of at least 15 W/(m·K). The substrate material may exemplarily comprise a ceramic material and may have a thermal conductivity of at least 20 W/(m·K), more typically at least a thermal conductively of at least 25 W/(m·K). Further, the substrate material may exemplarily comprise steel and may have a thermal conductivity of 30 W/(m·K) to 70 W/(m·K), more typically at least a thermal conductivity of 20 W/(m·K) to 50 W/(m·K). The thermal insulation element may have a thermal conductivity of less than 1 W/(m·K), typically of less than 0.5 W/(m·K), more typically of less than 0.1 W/(m·K) or even of less than 0.05 W/(m·K). The thermal insulation element may exemplarily have a plastic material and may specifically have a thermal conductivity of less than 1 W/(m·K), typically of less than 0.5 W/(m·K), more typically of less than 0.2 W/(m·K), more typically of less than 0.1 W/(m·K) or even less than 0.05 W/(m·K). Further, the thermal insulation element may exemplarily have air and may specifically have a thermal conductivity of less than 0.1 W/(m·K), typically of less than 0.05 W/(m·K), more typically of less than 0.03 W/(m·K).

In a further aspect of the present disclosure, a method for manufacturing at least one test element support is disclosed, the test element support comprising a heating element which is configured for heating at least one test element, the test element being configured for analytical examination of a sample. The method comprises the following method steps, which, typically, are performed in the given order. It shall be noted, however, that a different order is generally also possible. Further, one, more than one or even all of the method steps may be performed repeatedly. Further, two or more than two method steps may be performed in a timely overlapping fashion and/or in parallel. The method may comprise one or more additional steps, in addition to the method steps given below.

The method steps are as follows:
a) providing a substrate, the substrate being made of at least one substrate material,
b) providing at least one active area within the substrate, the active area being configured for being heated,
c) providing at least one non-active area within the substrate, the non-active area being located outside the active area,
d) providing at least one thermal insulation element separating the non-active area and the active area, wherein the thermal insulation element has a lower thermal conductivity than the substrate material, wherein the thermal insulation element is fully or partially embedded into the substrate,
e) providing at least one heater having at least one heater substrate, and
f) attaching the heater substrate to a back face of the substrate, the back face opposing a front face of the substrate contacting the test element.

For details and definitions of the method, reference may be made to the description of the heating element and the test element analysis system given above. Specifically, the method may be used for manufacturing the heating element according to the present disclosure, such as according to one or more of the embodiments given above and/or given in further detail below.

The test element support, the test element analysis system and the method according to the present disclosure provide a large number of advantages over known devices and methods. Thus, as an example, one or more thermal insulation elements may be placed around one or more active areas of the heating element. The active area may be defined as a virtual or functional area rather than a physical area, wherein, in the logical area, the requirements, e.g., for homogeneity of the heating, may be rather strict. By using the idea of the present disclosure, the homogeneity requirements may be fulfilled, by focusing the heat inside the active area of the heating element. The non-active area may be larger than the active area. Thus, as an example, the non-active area may be a surface area of the front face of the heating element which is larger by at least a factor of 1.2, such as at least 1.5 or even 2.5, than the active area of the test element. In the non-active area, the requirements for homogeneity of the heating generally are not as strict as in the active area.

The one or more thermal insulation elements specifically may be characterized by the fact that heat transportation through these one or more elements is significantly reduced as compared to the substrate material around these elements. Very simple embodiments for these thermal insulation elements may be holes, which may be produced rather easily.

With these one or more thermal insulation elements, the heat transport to other regions of the heating element may be prevented or at least reduced, and the homogeneity may be adjusted.

Another advantage of the design according to the present disclosure resides in the fact that a thermal capacity of the overall heating element may be reduced as compared to the situation without the one or more thermal insulation elements. Thus, thermal energy may be saved in the warm-up phase of the heating element. The overall time to reach a desired end temperature therefore may be reduced as compared to the case in which no thermal insulation elements are provided. This can result in an overall faster warm-up-phase of the instrument and thereby to an earlier "ready-to-use" status of the instrument which is specifically advantageous for Point of Care instruments in the critical ill area where you need very fast measurements and test results.

A further advantage of integrating the one or more thermal insulation elements into the heating element may be that the front face which may get into contact with the test element, such as the test strip, may be designed in a flat manner, such as by providing a flat surface, e.g., in case the one or more thermal insulation elements are flush with the front face.

As outlined above, the substrate material may be chosen from a plurality of materials. Generally, however, the substrate material may be adjusted to the desired properties. Thus, as an example, the realization of heat traps in ceramic heating elements is rather expensive. Therefore, even though this possibility still exists, it is typical to use stainless steel as a substrate material or at least as a part thereof. Another benefit of using stainless steel as a substrate material resides in the fact that stainless steel is more robust against shock loading than, e.g., ceramic materials.

In order to ensure that the front face, i.e., the contact surface with the test element such as the test strip, may also be electrically insulated, the front face of the heating element, specifically in case stainless steel is used, may be coated with one or more electrically insulating materials, such as with one or more electrically insulating layers, e.g., electrically insulating resins, lacquers or coatings, e.g., ceramic coatings. Thus, generally, the substrate and/or the substrate material may fully or partially be coated with one or more electrically insulating layers, such as with one or more electrically insulating layers of a resin, lacquer or ceramic coating. Other embodiments, however, are feasible.

Summarizing the findings of the present disclosure, the following embodiments are typical:

Embodiment 1: A heating element for heating a test element for analytical examination of a sample, the heating element having a substrate, the substrate being made of at least one substrate material, the substrate comprising at least one active area configured for being heated and at least one non-active area outside the active area, the active area and the non-active area being separated by at least one thermal insulation element, wherein the thermal insulation element has a lower thermal conductivity than the substrate material, wherein the thermal insulation element is fully or partially embedded into the substrate.

Embodiment 2: The heating element according to the preceding embodiment, wherein the active area and the non-active area are located in one plane of the heating element, specifically in one plane of the test element support.

Embodiment 3: The heating element according to any one of the preceding embodiments, wherein the thermal insulation element comprises at least one hole in the substrate, typically a hole selected from the group consisting of a round hole, a polygonal hole, a slot, an elongated hole.

Embodiment 4: The heating element according to the preceding embodiment, wherein the thermal insulation element comprises at least two holes, typically at least three holes, located in a row.

Embodiment 5: The heating element according to any one of the two preceding embodiments, wherein the substrate comprises at least one essentially flat front face and at least one essentially flat back face, wherein the hole extends from the front face to the back face.

Embodiment 6: The heating element according to any one of the three preceding embodiments, wherein the hole comprises rounded edges.

Embodiment 7: The heating element according to the preceding embodiment, wherein the front face of the substrate forms a supporting surface for the test element.

Embodiment 8: The heating element according to any one of the preceding embodiments, wherein the front face of the substrate is essentially free from protrusions.

Embodiment 9: The heating element according to any one of the preceding embodiments, wherein the thermal insulation element comprises a void in the substrate.

Embodiment 10: The heating element according to any one of the preceding embodiments, wherein the thermal insulation element is fully or partially made of at least one material selected from the group consisting of: air, a plastic material, a ceramic material, a composite material, such as a foam material.

Embodiment 11: The heating element according to any one of the preceding embodiments, wherein the active area is fully or partially surrounded by a virtual or non-virtual borderline, wherein the at least one thermal insulation element is located on the borderline.

Embodiment 12: The heating element according to any one of the preceding embodiments, wherein the heating element further comprises at least one heater.

Embodiment 13: The heating element according to the preceding embodiment, wherein the heater comprises at least one thermal resistor.

Embodiment 14: The heating element according to any one of the two preceding embodiments, wherein the heater comprises at least one heater substrate, wherein the heater substrate is attached to the substrate.

Embodiment 15: The heating element according to the preceding embodiment, wherein the heater substrate comprises at least one material selected from the group consisting of: a flexible circuit board, a circuit board.

Embodiment 16: The heating element according to any one of the two preceding embodiments, wherein the heater substrate is attached to a back face of the substrate, the back face opposing a front face of the substrate contacting the test element.

Embodiment 17: The heating element according to any one of the five preceding embodiments, wherein the heater comprises at least one electrical connector for electrically contacting the heater.

Embodiment 18: The heating element according to any one of the six preceding embodiments, wherein the heater is fully or partially embodied as a printed circuit board, typically a flexible printed circuit board.

Embodiment 19: The heating element according to any one of the seven preceding embodiments, wherein the heater comprises at least one thermal sensor element.

Embodiment 20: The heating element according to any one of the preceding embodiments, wherein the substrate is essentially flat.

Embodiment 21: The heating element according to any one of the preceding embodiments, wherein the at least one thermal insulation element is essentially flush with at least one surface of the substrate, specifically with a front face and/or a back face of the substrate.

Embodiment 22: The heating element according to any one of the preceding embodiments, wherein the substrate is fully or partially made of one or more of a plastic material, a metal or a ceramic material.

Embodiment 23: The heating element according to any one of the preceding embodiments, wherein the heating element further comprises at least one mounting element for mounting the heating element to at least one part of a test element analysis system.

Embodiment 24: The heating element according to the preceding embodiment, wherein the at least one mounting element comprises at least one mounting hole.

Embodiment 25: The heating element according to any one of the two preceding embodiments, wherein the at least one mounting element is located within the non-active area of the substrate.

Embodiment 26: The heating element according to any one of the three preceding embodiments, wherein at least two, typically at least four, mounting elements are provided, wherein the substrate is a flat substrate having an essentially rectangular shape with at least two, typically at least four, protrusions or ears protruding from the rectangular shape, wherein the mounting elements are located within the protrusions or ears.

Embodiment 27: The heating element according to any one of the preceding embodiments, wherein the heating element further comprises at least one connector region for electrically connecting the heating element to at least one electrical connector.

Embodiment 28: The heating element according to the preceding embodiment, wherein the connector region is located in the non-active area.

Embodiment 29: The heating element according to any one of the preceding embodiments, wherein the heating element further comprises at least one thermal sensor element.

Embodiment 30: The heating element according to the preceding embodiment, wherein the heating element comprises at least two thermal sensor elements, wherein at least one of the thermal sensor elements is located within the active area and wherein at least one of the thermal sensor elements located within the non-active area.

Embodiment 31: The heating element according to any one of the preceding embodiments, wherein the substrate material has a thermal conductivity at least 5 times the thermal conductivity of the thermal insulation element, more typically at least 10 times and even more typically at least 100 times.

Embodiment 32: The heating element according to any one of the preceding embodiments, wherein the substrate material has a thermal conductivity of at least 1 W/(m·K), more typically a thermal conductivity of at least 15 W/(m·K).

Embodiment 33: The heating element according to any one of the preceding embodiments, wherein the thermal insulation element has a thermal conductivity of less than 1 W/(m·K), typically of less than 0.5 W/(m·K), more typically of less than 0.1 W/(m·K) or even of less than 0.05 W/(m·K).

Embodiment 34: The heating element according to any one of the preceding embodiments, wherein the heating element comprises at least two active areas, wherein the active areas are separated by at least one thermal insulation element.

Embodiment 35: A test element support, wherein the test element support comprises at least one heating element according to any one of the preceding embodiments, wherein the test element support further comprises at least one heater.

Embodiment 36: The test element support according to the preceding embodiment, wherein the heater is located in an area opposing the active area of the substrate.

Embodiment 37: The test element support according to the preceding embodiment, wherein the heater is located on the back face of the substrate.

Embodiment 38: The test element support according to any one of the two preceding embodiments, wherein the active area contacts the test element.

Embodiment 39: The test element support according to the preceding embodiment, wherein the test element support is a test strip support.

Embodiment 40: The test element support according to any one of the two preceding embodiments, wherein the heater comprises at least one heater substrate, wherein the heater substrate is attached to the substrate.

Embodiment 41: The test element support according to any one of the three preceding embodiments, wherein the heater substrate is attached to a back face of the substrate, the back face opposing a front face of the substrate contacting the test element.

Embodiment 42: The test element support according to any one of the four preceding embodiments, wherein the active area of the heating element forms an integrated heating surface of the test element support.

Embodiment 43: The test element support according to the preceding embodiment, wherein the thermal insulation element is essentially flush with the integrated heating surface of the test element support.

Embodiment 44: The test element support according to any one of the six preceding embodiments, wherein the test element support is a flat test element support.

Embodiment 45: The test element support according to any one of the seven preceding embodiments, wherein the test element support provides a mechanical support for the test element.

Embodiment 46: The test element support according to any one of eight the preceding embodiments, wherein the test element support is configured such that the test element lies flatly on the front face of the substrate.

Embodiment 47: A test element analysis system for the analytical examination of a sample, the test element analysis system comprising at least one test element receptacle, wherein the test element analysis system further comprises at least one heating element according to any one of the preceding embodiments, wherein the heating element is arranged to heat at least one test element received at least partially in the test element receptacle.

Embodiment 48: The test element analysis system according to the preceding embodiment, wherein the test element analysis system further comprises at least one detector for detecting at least one analytical reaction of the sample with at least one test chemical comprised by the test element.

Embodiment 49: The test element analysis system according to any one of the preceding embodiments referring to a test element analysis system, the test element analysis system further comprising at least one test element.

Embodiment 50: The test element analysis system according to any one of the preceding embodiments referring to a test element analysis system, wherein the test element receptacle is arranged such that a test element received by the test element receptacle contacts both the at least one active area and the at least one non-active area of the heating element.

Embodiment 51: A method for manufacturing at least one heating element for heating a test element for analytical examination of a sample, the method comprising:
a) providing a substrate, the substrate being made of at least one substrate material,
b) providing at least one active area within the substrate, the active area being configured for being heated,
c) providing at least one non-active area within the substrate, the non-active area being located outside the active area, and
d) providing at least one thermal insulation element separating the non-active area and the active area, wherein the thermal insulation element has a lower thermal conductivity than the substrate material, wherein the thermal insulation element is fully or partially embedded into the substrate.

Embodiment 52: The method according to the preceding embodiment, wherein the method is for manufacturing a heating element according to any one of the preceding claims referring to a heating element.

In order that the embodiments of the present disclosure may be more readily understood, reference is made to the following examples, which are intended to illustrate the disclosure, but not limit the scope thereof.

In FIG. 1, a cross-sectional view of a simplified embodiment of a test element analysis system 110 for the analytical examination of a sample is shown. The test element analysis system comprises a housing 112 with user interfaces 114, such as a display 116 and one or more control elements 118 such as buttons. The test element analysis system 110 comprises at least one controller 120 which, as an example, may fully or partially be configured as an evaluation device for evaluating the analysis. The controller 120 may be connected to the user interfaces 114.

The test element analysis system 110 further comprises at least one test element receptacle 122 for receiving one or more test elements 124. The test element analysis system 110 further may comprise at least one detector 126, such as at least one optical detector 126, for detecting at least one analytical reaction of the sample with at least one test chemical 128 comprised by the test element 124, such as at least one test chemical 128 contained in at least one test field 130.

The test element 124 specifically may be designed as a test strip. For exemplary embodiments of test elements 124, reference may be made to the prior art described above. Other embodiments, however, are feasible. The detector 126 specifically may be an optical detector, such as a detector having at least one light source (not depicted) and at least one optical sensor, for performing remission measurements on the test field 130.

The test element analysis system 110 further comprises at least one test element support 108 comprising the heating element 132 for heating the test element 124. The heating element 132 comprises a front face 134, facing the test element 124, on which the test element 124 may rest, and, on an opposing side, a back face 136.

On the front face 134, an active area 138 is defined which faces the region of the test element 124 containing the test field 130. Outside the active area 138, a non-active area 140 is defined, as will be explained in further detail below. The active area 138 is separated from the non-active area 140 by at least one thermal insulation element 156, which will be explained in further detail below.

Further, the test element support 108 comprises at least one heater 142. The heater 142 may be located on the back face 136, as will be explained in further detail below with respect to FIG. 3B. The heater 142 comprises at least one heater substrate 143. Further, the heating element 132 comprises one or more thermal sensor elements 144 for detecting a temperature of the heating element 132. The heater 142 and the thermal sensor element 144 may both directly or indirectly be connected to the controller 120, as shown in FIG. 1.

Figure 2:
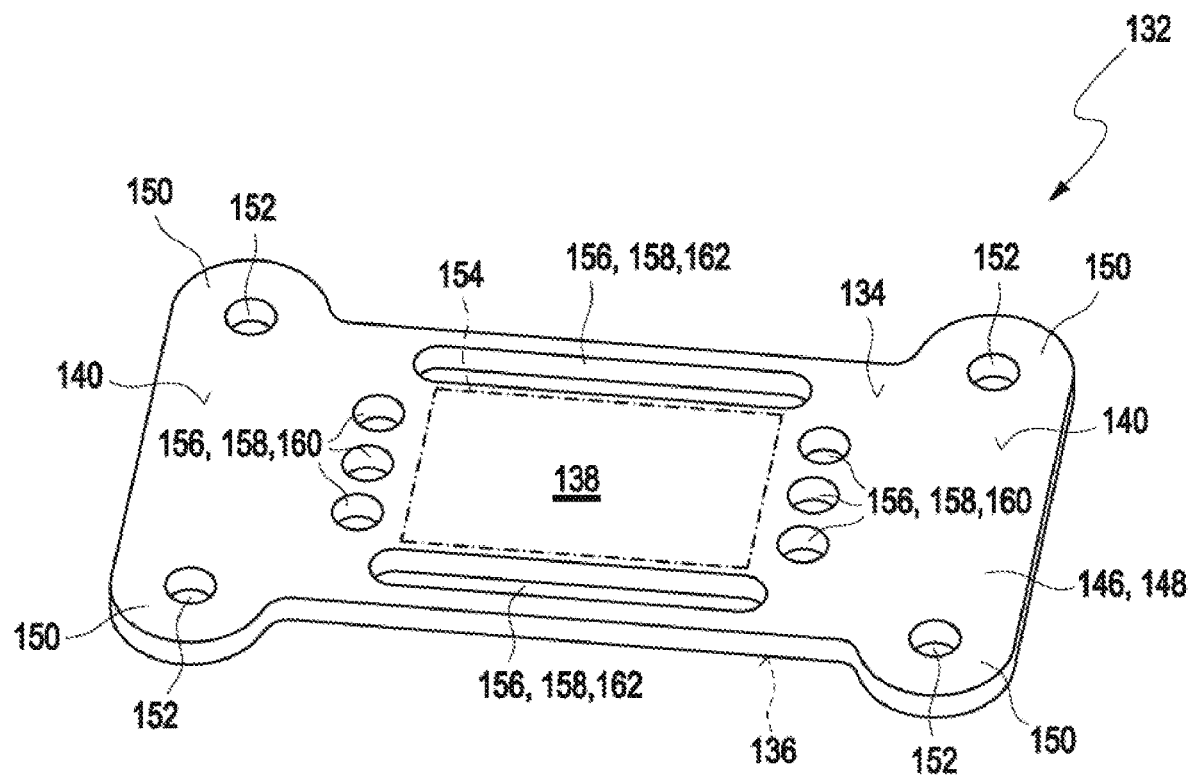
FIG. 2 shows a top view of a first exemplary embodiment of a heating element.

In FIG. 2, a top view onto a front face 134 of a first exemplary embodiment of a heating element 132 is shown. As shown therein, the heating element 132 may comprise a substrate 146 which fully or partially is made of at least one substrate material 148. The substrate specifically may be a flat substrate, with a plane front face 134 and a plane back face 136. The substrate 146 specifically may be essentially rectangular in shape, and may have, as an example, four protrusions 150 in the corners of the rectangle, also referred to as "ears". In these protrusions 150, one or more mounting elements 152 may be provided, for mounting the heating element 132 to the remaining parts of the test element analysis system 110, such as to a housing 112 of the test element analysis system 110. As an example, the mounting elements 152 may comprise mounting holes.

As discussed above in the context of FIG. 1, on the front face 134, the heating element 132 comprises at least one active area 138. The active area 138 of the heating element 132 may form an integrated heating surface 170 of the test element support 108. The active area 138 is an area which gets into contact with a side of the test element 124 in the region of the test field 130. The active area 138 is surrounded by at least one virtual borderline 154, along which, in this embodiment, a plurality of thermal insulation elements 156 are provided, in order to separate the active area 138 from the non-active area 140. The thermal insulation elements 156 have a lower thermal conductivity than the substrate material 148. For potential embodiments of Figures, reference may be made to the description given above.

As outlined above, the heating element 132 comprises at least one thermal insulation element 156 which separates the at least one active area 138 from the at least one non-active area 140. The heating element 132, however, may also comprise at least two active areas 138, which are separated from one another by at least one thermal insulation element 156. For details of potential embodiments of the thermal insulation element 156 separating the two active areas 138, reference may be made to the description above and to the embodiments shown in further detail below.

The substrate material 148, as an example, may comprise at least one metallic material, such as iron and, more typically, stainless steel. On the front face 134 and/or the back face 136, one or more electrically insulating layers may be provided.

The one or more thermal insulation elements 156 are fully or partially embedded into the substrate 146. A specifically simple and effective method for embedding and generating these thermal insulation elements 156 is to design these thermal insulation elements 156 as voids 158 in the substrate 146. These voids 158, as an example, may be designed as round through holes 160 and/or as one or more elongated through holes 162. As shown in FIG. 2, a combination of these options is possible, such as by placing round through holes 160 at the shorter sides of the rectangular-shaped borderline 154 and elongated through holes 162 at the longer sides of the borderline 154. It shall be noted, however, that other shapes of the borderline 154 are also feasible and, further, that other types of voids 158 are also possible. Further, it shall be noted that the thermal insulation elements 156, in this embodiment, are filled with air, which typically has a thermal conductivity of 0.0262 W/(m·K). The thermal conductivity of air is, thus, lower than the thermal conductivity of stainless steel which, typically, is in the range of 20 W/(m·K). It shall be noted, however, that other thermally insulating materials may be used. Thus, as an example, the voids 158 may also be filled with other types of thermally insulating materials, such as thermally insulating plastic materials and/or thermally insulating ceramic materials.

In FIGS. 3A and 3B, a second embodiment of a test element support 108 comprising a heating element 132 is shown. Therein, FIG. 3A shows a top view onto a front face 134, and FIG. 3B shows a bottom view, onto a back face 136. For most of the details, reference may be made to the description of the embodiment shown in FIG. 2 above. Again, the active area 138 may be defined by a virtual borderline 154, wherein, in this case, on one side of the borderline 154 a plurality of thermal insulation elements 156 in the form of a row of round through holes 160 is provided. Thus, virtually, the area above the row of round through holes 160 in FIGS. 3A and 3B may be defined as the active area 138, whereas the area below this row of round through holes 160 may be defined as the non-active area 140.

As can be seen in the back side view in FIG. 3B, the heating element 132 comprises a heater 142 which, in this exemplary embodiment, is designed as a thermal resistor 164. As an example, the heater 142 may comprise a printed circuit board, such as a flexible printed circuit board, which comprises the thermal resistor 164 and which is attached to the substrate 146 on the back face 136, in a region opposing the active area 138. As an example, the printed circuit board, in FIG. 3B symbolically denoted by reference number 166, may be glued to the back face 136, by a thermally conductive glue.

As outlined above, the heating element 132 may further comprise one or more thermal sensor elements 144. The one or more thermal sensor elements 144 may also be part of the printed circuit board 166, as shown in the exemplary embodiment of FIG. 3B. Thus, in this exemplary embodiment, one thermal sensor element 144 is located within the heater 142, on a side opposing the active area 138, whereas a second one of the thermal sensor elements 144 is located outside the heater 142, on a side opposing the non-active area 140. The thermal sensor elements 144 may be integrated into the printed circuit board 166.

The heater 142 and, specifically, the printed circuit board 166, may comprise at least one electrical connector 168 for electrically contacting the heater 142. The electrical connector 168 may also be used for electrically contacting the one or more thermal sensor elements 144.

The embodiments shown in FIG. 2 and in FIGS. 3A, 3B demonstrate options with one active area 138. As shown in a further embodiment depicted in FIG. 4, a plurality of active areas 138 may also be provided. Again, a front view, comparable to FIG. 3A and FIG. 2, is shown. Therein, three different active areas 138 are provided, in a row. In between the active areas 138, thermal insulation elements 156 are provided. Further, the thermal insulation elements 156 are also used for separating the active areas 138 from the surrounding non-active areas 140.

Figure 3:
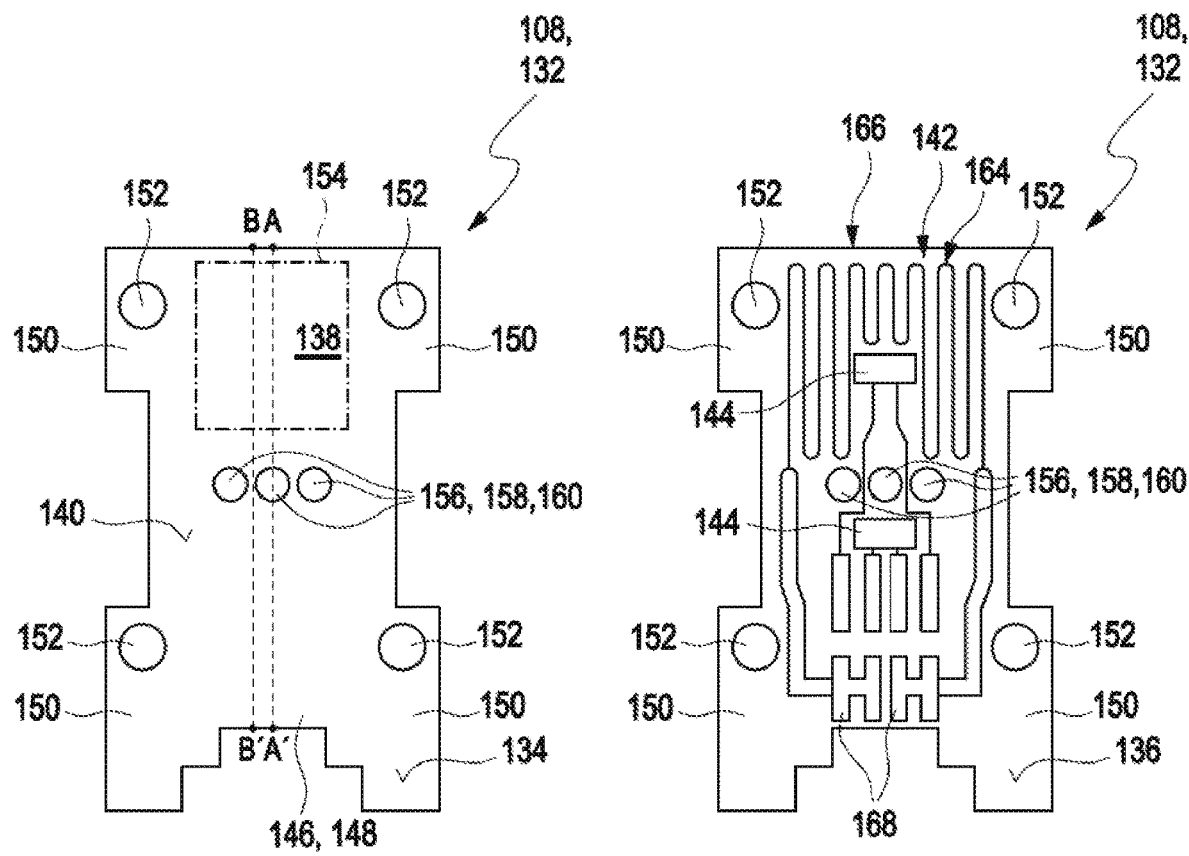
FIGS. 3A and 3B show a top (FIG. 3A) and bottom (FIG. 3B) view of a second exemplary embodiment of a heating element.
Figure 4:
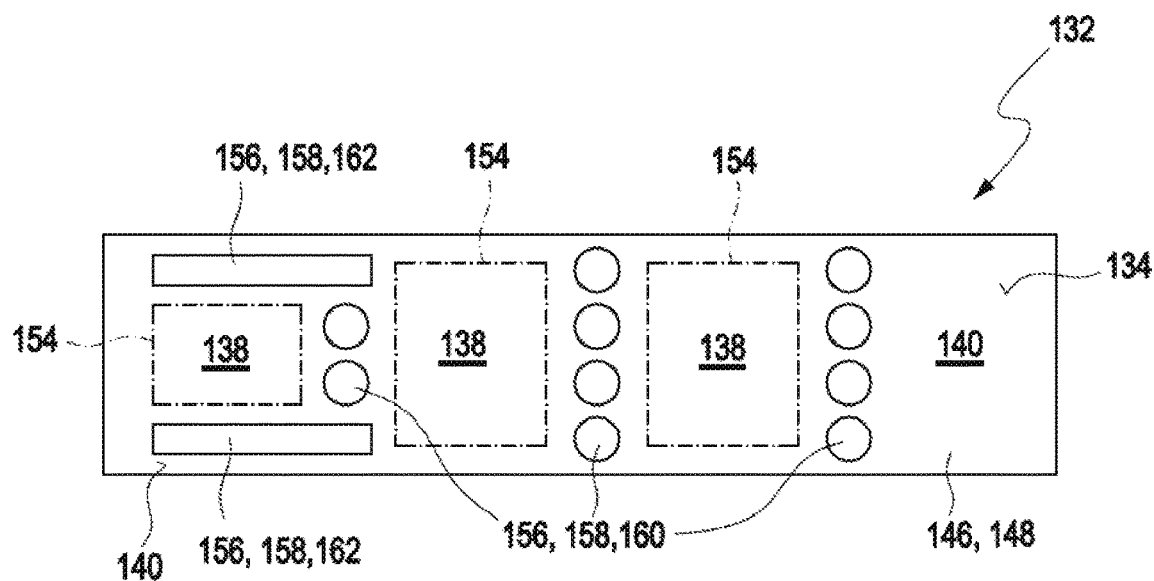
FIG. 4 shows a top view of a third exemplary embodiment of a heating element.

Thus, the embodiments shown in FIGS. 2 to 4 clearly demonstrate that a design of the placement, the number and the shape of the thermal insulation elements is possible, in order to provide a homogeneity of the at least one active area 138. The thermal profiles, for checking the homogeneity, may be calculated, such as by simulation calculations, or may be determined empirically.

Figure 5:
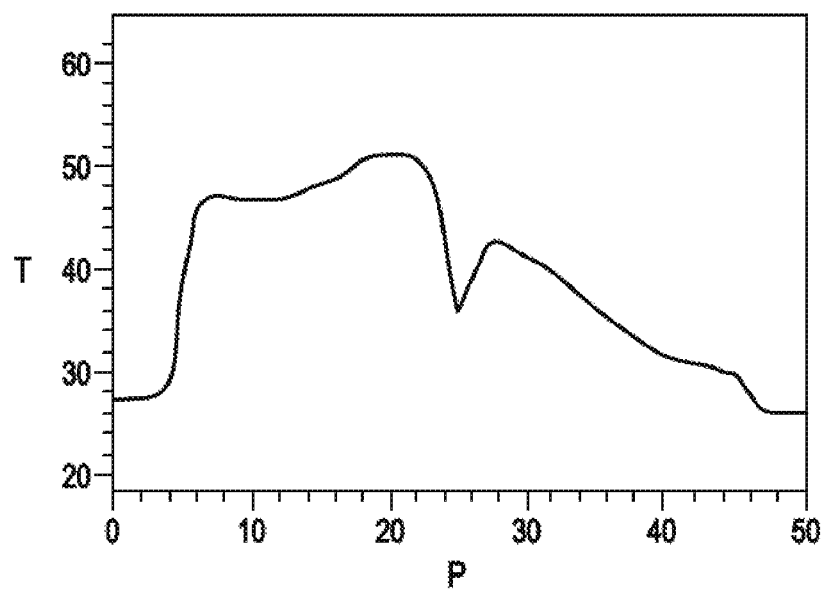
FIGS. 5A and 5B show two different temperature profiles of a heating element.
Figure 5:
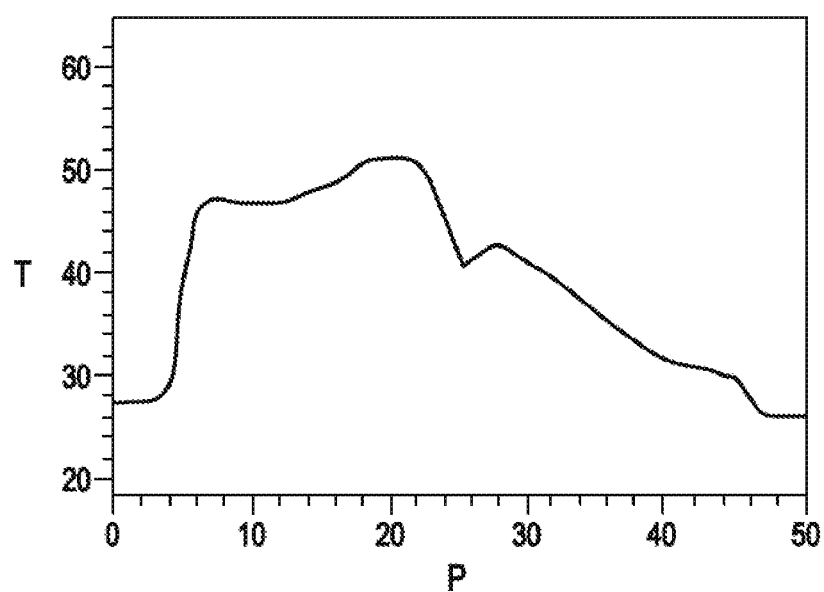

FIGS. 5A and 5B show temperature profiles of a heating element 132. Thereby, the heating element 132 may correspond to the heating element 132 for example as depicted in FIGS. 3A and 3B. Thus, for further details, reference may be made to the description of FIGS. 3A and 3B above. The temperature profiles were prepared on basis of a thermal image (not shown) of the heating element 132 made with an infrared camera VarioCAM® HR head 600 (InfraTec GmbH, Dresden, Germany). For preparing the temperature profile according to FIG. 5A a profile was placed in a direction along a longitudinal axis of the thermal image which corresponds to a direction along the heating element 132 according to the line A-A' as shown in FIG. 3A. The profile along the line A-A' was placed through an area of the thermal image which corresponds to a center of one of the thermal insulation elements 156 as depicted in FIG. 3A. Further, for preparing the temperature profile according to FIG. 5B a profile was placed in a direction along a longitudinal axis of the thermal image which corresponds to a direction along the heating element 132 according to the line B-B' as shown in FIG. 3A. This profile was placed through an area of the thermal image which corresponds to an area of a bridge between two thermal insulation elements 156 as depicted in FIG. 3A. The temperature profile as illustrated in FIGS. 5A and 5B show a temperature T in ° C. versus pixels P. The pixels have been equidistantly distributed along the lines A-A' and B-B'.

In these two temperature profiles (FIGS. 5A and 5b), a temperature drop, in the region of Pixel 22—which corresponds to the position of the insulation elements (156) in FIGS. 3A and 3B, is clearly observable. This significant drop is caused by the inventive insulation elements (156).

Beyond the area of this temperature drop, the temperature may further decrease in a linear manner or decreases in a linear manner. Such a linear decrease of the temperature directly at the virtual borderline (154) of the active area (138), without the significant drop, would be disadvantageous, due to requirements of homogeneity of the temperature inside of the active area (156).

LIST OF REFERENCE NUMBERS

- 108 test element support
- 110 test element analysis system
- 112 housing
- 114 user interface
- 116 display
- 118 control element
- 120 controller
- 122 test element receptacle
- 124 test element
- 126 detector
- 128 test chemical
- 130 test field
- 132 heating element
- 134 front face
- 136 back face
- 138 active area
- 140 non-active area
- 142 heater
- 143 heater substrate
- 144 thermal sensor element
- 146 substrate
- 148 substrate material
- 150 protrusion
- 152 mounting element
- 154 virtual borderline
- 156 thermal insulation element
- 158 void
- 160 round through hole
- 162 elongated through hole
- 164 thermal resistor
- 166 printed circuit board
- 168 electrical connector
- 170 integrated heating surface

What is claimed is:

1. A test element support, wherein the test element support is configured to bear or to hold up a test element as a separate element, wherein the test element support comprises:
   at least one heating element for heating the test element for analytical examination of a sample,
      the heating element having a substrate, the substrate being made of at least one substrate material, the substrate comprising at least one active area configured for being heated and at least one non-active area outside the active area,
      the active area and the non-active area being separated by at least one thermal insulation element, wherein the thermal insulation element has a lower thermal conductivity than the substrate material, wherein the thermal insulation element is fully or partially embedded into the substrate; and
   at least one heater, wherein the heater comprises at least one heater substrate, wherein the heater substrate is attached to the substrate, wherein the heater substrate is attached to a back face of the substrate, the back face opposing a front face of the substrate configured for contacting the test element, and wherein the active area of the heating element forms an integrated heating surface of the test element support.

2. The test element support according to claim 1, wherein the thermal insulation element comprises at least one hole in the substrate.

3. The test element support according to claim 2, wherein the substrate comprises at least one essentially flat front face and at least one essentially flat back face, wherein the hole extends from the front face to the back face.

4. The test element support according to claim 1, wherein the thermal insulation element is fully or partially made of at least one material selected from the group consisting of: air, a plastic material, a ceramic material, a composite material.

5. The test element support according to claim 1, wherein the heater is fully or partially embodied as a printed circuit board.

6. The test element support according to claim 1, wherein the heater is located in an area opposing the active area of the substrate.

7. The test element support according to claim 1, wherein the front face of the substrate is essentially free from protrusions.

8. The test element support according to claim 1, wherein the heating element further comprises at least one mounting element for mounting the heating element to at least one part of a test element analysis system.

9. The test element support according to claim 1, wherein the heating element further comprises at least one thermal sensor element.

10. The test element support according to claim 1, wherein the substrate material has a thermal conductivity at least 5 times the thermal conductivity of the thermal insulation element.

11. A test element analysis system for the analytical examination of a sample, the test element analysis system comprising at least one test element receptacle, wherein the test element analysis system further comprises at least one test element support according to claim 1, wherein the test element support is arranged to heat at least one test element received at least partially in the test element receptacle.

12. The test element analysis system according to claim 11, wherein the test element analysis system further comprises at least one detector for detecting at least one analytical reaction of the sample with at least one test chemical comprised by the test element.

13. The test element analysis system according to claim 11, the test element analysis system further comprising at least one test element.

14. The test element support of claim 1 wherein a test element supported by the test element support is received against the front face of the substrate.

15. The test element support of claim 1 in which the front face of the substrate comprises a single, flat plane.

16. A test element assembly comprising:
a test element support according to claim 1; and
a test element received against the front face of the substrate.

* * * * *